United States Patent [19]

Blacker et al.

[11] Patent Number: 5,508,444
[45] Date of Patent: Apr. 16, 1996

[54] CYCLIC COMPOUNDS

[75] Inventors: Andrew J. Blacker, North Yorks; Martin Brown, Huddersfield; Martin C. Bowden, West Yorks, all of England

[73] Assignee: Zeneca Limited, London, England

[21] Appl. No.: 302,648

[22] PCT Filed: Mar. 12, 1993

[86] PCT No.: PCT/GB93/00523

§ 371 Date: Nov. 17, 1994

§ 102(e) Date: Nov. 17, 1994

[87] PCT Pub. No.: WO93/17994

PCT Pub. Date: Sep. 16, 1993

[30] Foreign Application Priority Data

Mar. 13, 1992 [GB] United Kingdom ............... 9205505

[51] Int. Cl.[6] ................. C07D 313/00; C07C 69/74
[52] U.S. Cl. .................. 549/268; 549/285; 549/299; 549/354; 549/389; 560/128; 558/428; 558/430; 554/111; 554/221
[58] Field of Search ............... 560/128; 554/111, 554/221; 558/428, 430; 549/268, 285, 299, 354, 389

[56] References Cited

U.S. PATENT DOCUMENTS 5,216,083  6/1993  Grubbs et al. ............... 525/342

FOREIGN PATENT DOCUMENTS 364152  4/1990  European Pat. Off. .
379300  7/1990  European Pat. Off. .

OTHER PUBLICATIONS

Demarinis et al: "Synthesis of trans-2, 3-dihydroxy-2, 3-dihydrobenzoic acid and related substances from 4-carbo-tert-butoxyoxepin", Journal of the American Chemical Society, vol. 96, No. 4, Feb. 20, 1974, pp. 1193–1197.

Gibson, et al: "Microbial Degradation of Aromatic Hydrocarbons", The Microbial Degradation of Oil Pollutants, pp. 33–38 (1973).

Joseph–Nathan, P et al CA: 5430a (1966).

*Primary Examiner*—C. Warren Ivy
*Assistant Examiner*—Amelia Owens
*Attorney, Agent, or Firm*—Cushman Darby & Cushman

[57] ABSTRACT

Novel substituted cis-1,2-dihydroxy-cyclohexadiene compounds, useful as intermediates in the production of compounds for use as intermediates in the production of agrochemicals and pharmaceuticals, and a microbial process for the preparation thereof.

13 Claims, No Drawings

CYCLIC COMPOUNDS

This application is a 371 of PCT/GB93/00523 filed Mar. 12, 1993.

This invention relates to cyclic compounds and to a process for making them. The compounds are useful intermediates in the fields of agrochemicals and pharmaceuticals.

Certain cis 1,2-dihydroxycylohexadienes are useful in the preparation of novel polymers. In our European Patent Specification No. 76606 B we disclose a process for the production of such dihydroxy cyclohexadienes from aromatic compounds using mutant strains of the species *Pseudomonas putida*, in particular mutants of *P. putida* strains NCIB 11767 and NCIB 11680. The enzyme which catalyses the reaction involved in this process is an aromatic dioxygenase which catalyses a reaction between certain aromatic compounds and oxygen for example, the reaction below between benzene and oxygen

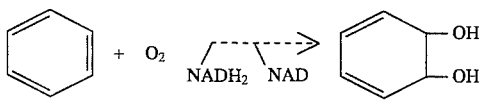

When strains such as *P. putida* NCIB 11767 and NCIB 11680 are fed with aromatics, the dihydroxy cyclohexadiene compounds do not accumulate since they are rapidly further oxidised via catechols to products of intermediary metabolism. However, in our European Patent No. 76606-B we describe how mutants of these microorganisms may be produced which are unable to oxidise the dihydroxy cyclohexadienes and these as a result accumulate when such mutants are exposed to aromatic substrates. Some of these mutants must be grown in the presence of benzene or toluene if the activity of the aromatic dioxygenase enzyme needed to convert aromatics to dihydroxy cyclohexadienes is to be induced.

The process of our European Patent 76606-B, particularly when carried out using microbial cells produced by the method of European Patent No. 250 122 B, enables conversions of aromatic compounds to be achieved to produce some interesting new cyclic dihydroxy compounds. In our EP-A-364 152 we disclose compounds of the formula

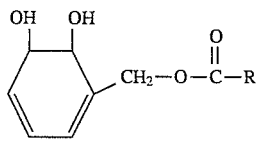

where R is an alkyl or substituted alkyl group, and a process for preparation of such compounds using *P. putida*.

The process of EP-A-364 152 involves crystalising the cyclic dihydroxy compounds under conditions of extremely low temperatures (for example, −78° C.) which are not practical or economic for the preparation of large quantities of the compounds for use in the preparation of, for example, agrochemicals or pharmaceuticals.

Surprisingly, it has been found that preparation of the novel compounds of the present invention can by achieved with much less difficulty and more economically by the process of the present invention.

According to the invention there is provided a cyclohexadiene compound of formula (I) or (II)

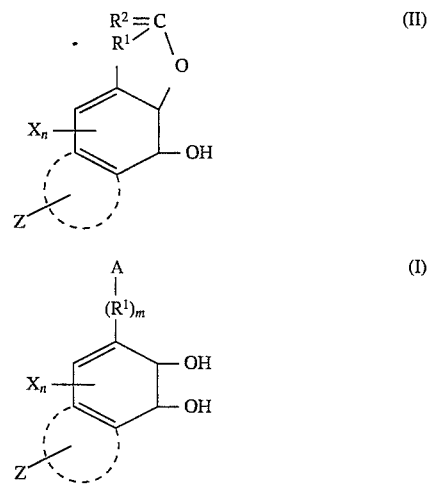

wherein A is a carboxylic ester or CN; $R^1$ is lower alkylene in formula (II) and methylene in formula (I) both optionally carrying one or more non-interfering substituents; $R^2$ is O or NH or $NR^3$; $R^3$ is $C_{1-4}$ alkyl; X is a non-interfering substituent; Z is an optional group comprising a 5- or 6-membered carbocyclic ring which is optionally substituted; m is 0 or 1; and n is 0–3.

In the compounds of formula (I) A is a carboxylic ester having the formula —C(O)—O—R, preferred examples are those in which R is straight or branched chain $C_1$-$C_{10}$ alkyl, particularly $C_{1-4}$ alkyl, for example, methyl, ethyl, n- and iso-propyl, n-, iso-,sec- and tertiary-butyl.

In the compounds of formula (I) $R^1$ is methylene and is optionally substituted one or more non-interfering substituents including halogen, particlularly fluorine, chlorine, bromine and iodine, $C_{1-6}$ alkyl, particularly, methyl, ethyl, n-, isopropyl, n-, iso-, sec- and tertiary-butyl, $C_{3-6}$ cycloalkyl especially cyclohexyl, $CF_3$, CN, $NO_2$, phenyl or phenyl substituted with substituents as defined for X below, $CO_2R$ where R is as defined above, OH, $OR^4$, SH, $SR^4$, $NHR^4$, $NR^4R^4$, O, NOH, $NOR^4$, $CH_2$, $CR^4H$ and $CR^4R^4$.

Where $R^1$ in formula (II) is lower alkylene it is preferably $C_{1-4}$ alkylene, especially methylene or ethylene. $R^1$ is optionally substituted with suitable non-interfering substituents including halogen, particlularly fluorine, chlorine, bromine and iodine, $C_{1-6}$ alkyl, particularly, methyl, ethyl, n-, iso-propyl, n-, iso-, sec- and tertiary-butyl, $C_{3-6}$ cycloalkyl especially cyclohexyl, $CF_3$, CN, $NO_2$ , phenyl or phenyl substituted with substituents as defined for X below, $CO_2R$ where R is as defined above, OH, $OR^4$, SH, $SR^4$, $NHR^4$, $NR^4R^4$, O, NH, $NR^4$, NOH, $NOR^4$, $CH_2$, $CR^4H$ and $CR^4R^4$.

The substituent $R^4$ is straight or branched chain $C_{1-6}$ alkyl, preferably methyl, ethyl, n- or iso-propyl, n-, iso-, sec-, or tertiary-butyl, optionally substituted with halogen, preferably fluorine or chlorine, alkoxy, preferably $C_{1-4}$ alkoxy, especially methoxy, alkylsulphide, preferably $C_{1-4}$ alkylsulphide or $R^4$ is alkylcarbonyl, preferably $C_{2-6}$ alkylcarbonyl.

When $R^2$ in formula (II) is $NR^3$, $R^3$ is preferably methyl or ethyl.

The substituent X is preferably selected from the group, halogen, particlularly fluorine, chlorine, bromine and iodine, $C_{1-6}$ alkyl, particularly methyl, ethyl, n-, iso-propyl, n-, iso-, sec-and tertiary-butyl, $C_{3-6}$ cycloalkyl, $CF_3$, CN, $NO_2$, phenyl, $CO_2R^4$, OH, $OR^4$, SH, $SR^4$ and $NR^4R^4$. $R^4$ is as previously defined. Particularly preferred are compounds of formula (I) or (II) where at least 1, preferably 1 or 2 of the X substituents is/are fluorine.

When Z is present it is a five or 6-membered carbocyclic ring, and it is preferably benzene or benzenoid. It may also be a saturated ring, that is to say, cyclopentyl or cyclohexyl. Z can be optionally substituted with a substituent selected from the group, halogen, particlularly fluorine, chlorine, bromine and iodine, $C_{1-6}$ alkyl, particularly methyl, ethyl, n-, iso-propyl, n-, iso-, sec and tertiary-butyl, $CF_3$, CN, $NO_2$, phenyl optionally substituted with substituents as defined for X above, $CO_2R_4$, OH, $OR^4$, SH, $SR^4$ and $NR4R^4$, R4 is as previously defined.

Particularly preferred compounds of the invention are those in which Z is not present.

With reference to formula (I) particularly preferred compounds are those compounds where A is —C(O)—O—R or —CN; m is 0 or 1; $R^1$ is methylene optionally substituted with halogen, $C_{1-6}$ alkyl, $CF_3$, CN, $NO_2$, phenyl or phenyl substituted with substituents as defined for X above, $CO_2R$, OH, $OR^4$, SH, $SR^4$, $NHR^4$, $NR^4R^4$, O, NOH, $NOR^4$, $CH_2$, $CR^4H$ and $CR^4R^4$; X is selected from the group, halogen, $C_{1-6}$ alkyl, $CF_3$, CN, $NO_2$, phenyl, $CO_2R^4$, OH, $OR^4$, SH, $SR^4$, $NR^4R^4$; $R^4$ is as defined above; and n is 0–3.

With reference to formula (II) particularly preferred compounds are those in which $R^1$ is methylene optionally substituted with halogen, $C_{1-6}$ alkyl, $CF_3$, CN, $NO_2$, phenyl or phenyl substituted with substituents as defined for X above, $CO_2R$, OH, $OR^4$, SH, $SR^4$, $NHR^4$, $NR^4R^4$, O, NH, $NR^4$, NOH, $NOR^4$, $CH_2$, $CR^4H$ and $CR^4R^4$; $R^2$ is O; X is selected from the group, halogen, $C_{1-4}$ alkyl, $CF_3$, CN, $NO_2$, phenyl, $CO_2R^4$, OH, $OR^4$, SH, $SR^4$, $NR^4R^4$; $R^4$ is as defined above; and n is 0–3.

Especially preferred are the compounds of formula (I) and (II) wherein m is 1, A is —C(O)—O—R, R is $C_{1-4}$ alkyl, $R^1$ is $CH_2$ or CHOH, $R^2$ is O and either n is O or at least one X is halogen.

Further especially preferred compounds of formula (I) are those wherein m is O, A is —C(O)—O—R, R is methyl or ethyl and either n is O or at least one X is halogen.

Compounds of formula (I) and (II) as defined above are optically active and the enantiomers are preferred compounds of the invention. For example for the diol in which $R^1$ is $CH_2$ and n is O there is an excess of the 2R, 3S enantiomer. The oxygens are linked to the ring preferably in a cis configuration. The identity of the X substituent on the compound may change the Cahn-Ingold-Prelog R,S nomenclature but it will be apparent to the skilled person that such compounds conform to the 2R, 3S general configuration.

The invention provides processes for producing the compound by stages including hydroxylating enzymatically a corresponding benzenoid compound substrate. The enzyme, aromatic dioxygenase, can be used as such or with the aid of a host microorganism carrying it, whether induced or constitutive. One such host microorganism is any one of the chloridazon-degrading bacteria described by Wegst et al., Biochem J. 1981, 194, 674–684. A preferred host microorganism is a strain of *Pseudomonas putida*, for example as described in our EP-A-76606 or EP-A-250122.

Another suitable host is a bacterium into which the gene for the aromatic dioxygenase enzyme has been introduced. Such a host may be *P. putida* or other Pseudomonas, or an organism already known for organic oxidations (e.g. Nocardia) or a more remote bacterium for example *E. coli*. The process comprises supplying a corresponding benzenoid compound, oxygen and an energy source to the microorganism.

According to a further aspect of the invention there is provided a process for the preparation of compounds of formula (I) and (II) which comprises supplying the corresponding benzenoid compound, oxygen and an energy source to a microorgansim in which the aromatic dioxygenase enzyme has been introduced.

Examples of suitable energy sources include alcohols such as ethanol, carboxylic acids such as pyruvic acid and carbohydrates such as glucose. Preferred energy sources are ethanol and glucose.

The strain of *P. putida* preferably is not capable of growth on benzene or or substituted benzenes or the said dihydroxy compound, and is derived from a strain of *P. putida* capable of growth on benzene or toluene.

It may for example be the product of inducing aromatic dioxygenase enzyme in a first mutant strain derived from *P. putida* strain NCIB 11680 or NCIB 11767 deposited at the National Collection of Marine and Industrial Bacteria, Torrey Research Station, Aberdeen, Scotland, UK.

Very suitable first mutant strains may be prepared by treating *P. putida* NCIB 11680 or preferably *P. putida* NCIB 11767 under mutating conditions and selecting strains which are incapable of utilising toluene or benzene as a sole source of carbon for growth and which, when grown in a liquid medium containing pyruvic acid as a carbon source in the presence of benzene or toluene, excrete a substance which has a UV absorbance peak at respectively 260 or 265 nm. This mutation may be effected by chemical means for example by treatment with N-methyl-N-nitroso-N'-nitroguanidine (NTG), e.g. as described by Ornston, Journal of Biological Chemistry, 1966, Volume 241 pages 3800–3810. Alternatively, physical mutation may be effected by electromagnetic radiation, e.g. UV light.

If the enzyme is produced constitutively, the strain may be derived from said first mutant by further mutation.

A constitutive mutant strain is suitably prepared by treating the first mutant strain (especially of *P. putida* NCIB 11767) under mutating conditions and selecting strains which, after growth in the absence of an aromatic compound, produce cyclic dihydroxy compounds from aromatic compounds. For example the cells after mutation can be grown on solid agar containing pyruvic acid or glucose as carbon source, and the colonies on the agar plates sprayed with a solution of catechol in water. Colonies which rapidly turn yellow/green are constitutive for an enzyme which converts catechol into 2hydroxymuconic semialdehyde (Nozaki, Topics in Current Chemistry (English Review) 1979, Volume 78, pages 145–186). This enzyme catalyses one of the steps in the oxidative degradation of benzene in *P. putida* NCIB 11680 and *P. putida* NCIB 11767 and is linked in its expression to the enzyme which converts benzene to the cyclic dihydroxy compound.

If the constitutive mutant strain is to be grown on a carbohydrate carbon source such as glucose in the presence for example of casamino acids, preferred strains not susceptible to catabolite repression may be obtained by further mutation. Such strains can be detected by growing colonies of the mutated constitutive strains on an agar medium which contains a mixture of glucose and casamino acids as carbon sources: the colonies which turn yellow/green on exposure to catechol comprise the improved constitutive strain.

The preparation of these constitutive strains is described in more detail in our EP-A-253485.

First mutant cells may be grown in conventional growth media as a continuous, batch or fed-batch technique.

The medium in which the strains may be grown comprises an aqueous mineral salts solution and a carbon source, for example, pyruvic acid glucose or ethanol. The concentration of carbon source is generally between 1 and 20% (w/w). Oxygen must be present during the growth period. The temperature of the medium during the growth period normally will be in the range 25° to 35° C. The pH of the medium is kept within the range 5.5 to 8.0 during growth, preferably 6.5 to 7.5. The size of the culture can be for example between 1.5 and 200000 litres.

If dioxygenase enzyme is to be induced, there may be present also an inducer compound, for example benzene or a substituted benzene or more suitably, one or more of cyclohexane, cyclohexanol, cis 1,2-dihydroxy-cyclohexa-3.5diene, furan, thiophene, benzofuran, cyclohexadiene, coumarin and mesitylene. Particularly preferred inducer compounds are pyridine and methyl-substituted pyridines. Induction may be in more than one stage, for example a first induction with benzene and a second with e.g. pyridine.

Following the growth period the cells are used in the hydroxylation stage. The cells may be harvested, for example by centrifugation or flocculation, or may be used directly. If harvested, they are resuspended in a mineral salts solution which does not support significant cell growth e.g. phosphate buffer solutions which lacks or contains little of one or more essential elements. Typically the concentration of resuspended cells is 1 to 30 g dry weight per litre. The cells are kept at a 20° to 40° C. and the pH maintained between 6.5 and 8.5. Oxygen is supplied to the cell suspension such that the oxygen tension is kept at greater than 1% of saturation. The energy source supplied to the cell suspension is maintained at a concentration preferably between 0.05 and 0.5% (w/w).

The substrate may be supplied to the cell suspension as a solution in an inert solvent if it is a solid, or as a salt if it is an acid or as a neat liquid if it is a liquid. If the lactonic compound is required, a mixture of acid and ester can be added, possibly with an inert solvent.

The rate of addition of the substrate to the culture is typically about 0.5 to 10 g per g dry weight of cells per hour. The rate of addition of the energy source may vary during the conversion but is typically in the range 0.1 to 2.0 g per g dry weight of cells per hour. The productive lifetime of the cell suspension is typically between 5 and 50 hour. After this period the cells are removed by centrifugation and/or flocculation. Fresh cells may be added to the supernatant liquor and the process repeated. At the end of the process the supernatant liquor typically contains between 10 and 100 g per litre of product.

The cyclic dihydroxy compounds are preferably extracted from the aqueous reaction mixture by solvent extraction. Examples of extraction solvents include ethyl acetate, methyl isopropylketone and methylene chloride. A continuous extraction procedure may be employed. Alternatively, the aqueous medium after separation of the cells may be evaporated and the residue dissolved in e.g. methanol, ethanol or methylene chloride. If there is any residual acid in the residue, precautions such as cooling, buffering or thorough drying should be taken to prevent a catalytic reaction. Preferably then an organic base should be added, for example a tertiary amine such as triethylamine or pyridine.

A particular advantage of the process of preparation of compounds of the present invention is that the compounds of formula (I) convert at room temperature by crystallisation into the compounds of formula (II).

Thus, the present invention also provides one or more further stages of converting the cyclohexadiene compounds of formula (I) as follows:

(a) to the corresponding lactonic compound of formula (II);

(b) to the corresponding carboxylic acid or salt of formula (V);

(c) to the corresponding arylboronate compound.

Conversion (a) is carried out in the presence of a catalytic quantity of acid, and either happens at room temperature or by gently heating the ester or nitrile. The acid may be present in the residue in which case the reaction proceeds without further intervention, or may be added, for example, p-toluene sulphonic acid, benzoic acid, sulphuric acid or phosphoric acid.

Conversion (b) can be carried out by treating the ester of formula (I) or lactonic compound of formula (II) with alkali, for example the hydroxide or carbonate of sodium or potassium. The resulting salt can be acidified to give the carboxylic acid, but this must be done with care, since acid also catalyses dehydration to form the aromatic compound of formula (VII).

Conversion (c) is described in our EP-A-379 300.

Compounds of formula (I), (II) and (V) can be converted in a further process step to the corresponding coumaranone of formula (VI). The conversion can be carried out by acidification or thermal dehydration or both. The acid used is preferably a polyphosphoric acid. Usually a temperature over 140° C., for example up to 180° C., is needed for a convenient rate of reaction. Dehydration may be applied to the solid or to a solution, for example in a liquid having a boiling point in the above temperature range, such as mesitylene.

Thus, in a further aspect of the invention there is provided a process for the preparation of compounds of formula (VI):

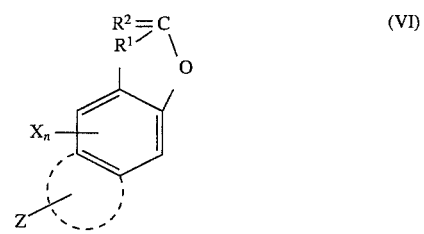

which comprises (a) preparing the compounds of formula (I) or (II) by supplying the corresponding benzenoid compound, oxygen and an energy source to a microorgansim in which the aromatic dioxygenase enzyme has been introduced; and (b) either acidifying or thermally degrading the product of (a) to form the compound of formula (VI).

The compounds of formula (I) or (II) can be converted to the corresponding catechols or hydroxycoumaranones by enzymatic or chemical methods, for example by means of a transition metal catalyst (especially metallic palladium or platinum), possibly in the presence of a hydrogen acceptor such as an oxidant, for example potassium ferricyanide, or a hydrogenisable compound e.g. cyclohexene.

The compounds of formula (VII) can be formed directly from compounds of formula (I) or (V) by treatment with acid or indirectly from compound VI by treatment with alkali. If sufficient alkali is used, the phenolic OH is also neutralised. It is not usually practicable to make the free carboxylic acid of formula VII, since ring-closure readily takes place on acidification.

Thus, the invention provides in particular a process of making a salt of a 2-hydroxy phenylalkanoic acid of formula (VII) from the corresponding phenylalkanoic acid by microbiological hydroxylation followed by dehydration and aromatisation: characterised by (a) converting the corresponding phenylalkanoic acid to an ester (III) having a melting point under 35° C.;

(b) feeding the resulting ester (III) to the microbiological treatment;

(c) recovering the resulting hydroxylated ester (I) by solvent extraction;

(d) ring-closing the hydroxylated ester (I) by ester-interchange;

(e) dehydrating the resulting lactone (II);

(f) ring-opening the lactone (II) by treatment with alkali to give the salt (VII);

(g) converting the resulting salt (VII) to salt having the required cation, if such cation was not used in the alkali in stage (f).

A further advantage of the process of the present invention is that it is particularly useful for the preparation of 2-hydroxy phenylalkanoic acid. According to Wegst et al., (Blochem J 1981, 194, 674–684) phenyl acetic acid can be hydroxylated directly to the dihydroxy acid. However, their method is inconvenient in that the starting acid, being a solid of low solubility in water, has to be added as a solid or salt: thus there are measuring difficulties or extraneous materials are introduced. Further, the product is also a salt and thus has a partition coefficient very unfavorable to extraction by a water-insoluble solvent. The usual methods to isolate the carboxylate from water would be to acidify and extract into a water-insoluble solvent. In the present invention adicification may lead to undesirable aromatisation of the product (conversion a or b).

The compounds of the invention are useful intermediates for the preparation of pharmaceuticals and agrochemicals. Therefore, in a further aspect of the invention there is provided the use of the compounds of formula (I) and (II) as defined above as intermediates in the preparation of the corresponding lactones, arylboronates, carboxylic acids or salts thereof, coumaranones, hydroxycoumaranones, monohydric phenolcarboxylates, 2-hydroxy phenylalkanoic acids and salts thereof, catechols, and optionally the use of any of the said intermediates in the preparation of agrochemical or pharmaceutical products. The invention is further described by reference to examples in which NMR is nuclear magnetic resonance spectroscopy, MS is mass spectrometry, $[\alpha]_D$ is optical rotation (measured using a Polartronic Universal machine).

PREPARATION OF MUTANT STRAINS

Growth Media used

1 Bauschop and Elsdon's as described in Journal of General Microbiology, 1960, Volume 23, pages 457–469.

2 Luria liquid as described in "Experiments in Molecular Genetics" by J H Miller, published by Cold Spring Harbor Laboratories, New York, 1972.

Preparation of Mutant A

*P. putida* NCIB 11767 was grown to early exponential phase in medium 2. The cells were harvested by centrifugation and resuspended at a concentration of 0.2 g dry cell weight per litre in 20 ml of 25 mM citric acid-sodium titrate buffer pH 5.5 containing i mg of NTG. After 45 min at 30° C. the cells were harvested by centrifugation, washed twice with medium 1 and then grown overnight in this medium containing 0.3% w/v sodium pyruvate at 30° C. After serial dilution, cells were plated on a medium 1 agar containing 0.3 mM (0.033% w/v) sodium pyruvate and incubated in 1 litre paint tins each containing 0.5 ml benzene in a vial. After 3 days at 30° C., 144 colonies less than 0.5 mm diameter were picked off and regrown on a 0.2% w/v sodium pyruvate medium 1 agar. These were "first mutant".

Induction of aromatic dioxygenase 90 of these mutants were screened in medium 2 plus sodium pyruvate for the production from benzene of a compound absorbing at 260 nm. One which gave a supernatant maximum absorbance at 260 nm of 37 is hereinafter referred to as mutant B.

Preparation of Mutant C (Constitutive)

*P. putida* NCIB 117617 was grown and NTG-treated as in the preceding paragraph. The NTG-treated cells were washed, diluted and plated onto $1.8 \times 10^5$ colonies of medium 1 agar plus 10 mM (0.011%w/v) sodium pyruvate. After two days at 30° C., colonies were sprayed with a solution of catechol in water (0.5 molar) and 35 that turned yellow/green after 5 min were selected and grown overnight in 16 ml of medium 1 plus 0.5% w/v sodium pyruvate. Cells were harvested and resuspended in 10 ml of 25 mM potassium phosphate buffer, pH 7.8, containing 0.4% w/v ethanol. These cultures in 250 ml conical flasks were incubated overnight, each in the presence of 0.5 ml toluene. Supernatants were examined for compounds absorbing at 265 nm. A constitutive mutant (C) which gave an absorbance of 250 was selected.

Preparation of Mutant D (constitutive)

Mutant D was grown at 30° C. in 20 ml of medium 2 to early exponential phase and, after harvesting, cells were resuspended to 40 ml of 0.1 molar $MgSO_4 7H_2O$. A 5 ml aliquot was UV-irradiated in a glass petri dish for 45 sec at a dose of $1.6\mu W/cm^2 \times 100$. The cells were then grown in the dark in five 20 ml aliquots of medium 1 plus 10 mM (0.011% w/v) sodium pyruvate.

GENERAL SYNTHESIS SCHEME

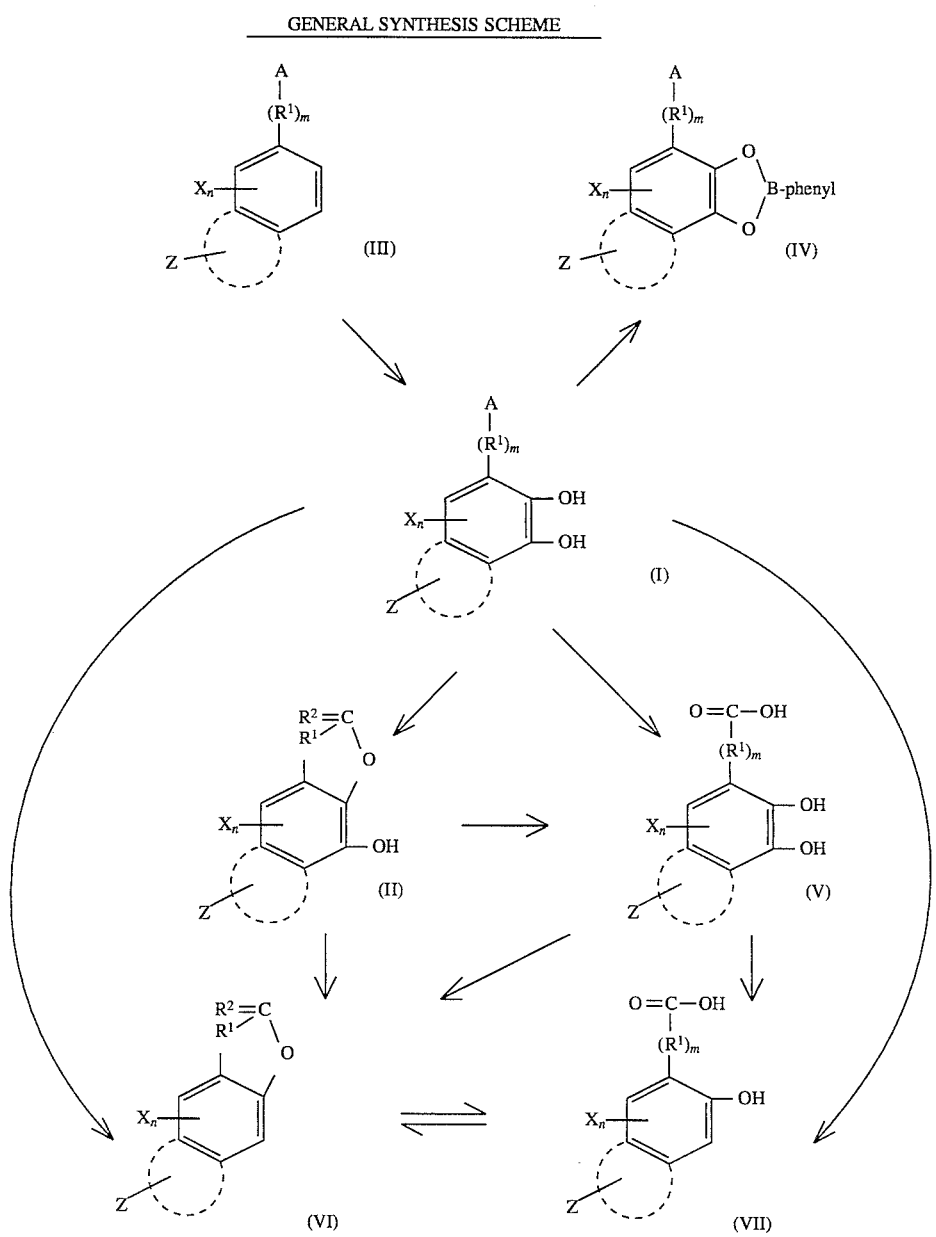

After 2 days at 30° C. cultures were serially diluted and plated onto 4×104 colonies of medium 1 plus 75 mM glucose and 1% w/v vitamin free casamino acids (ex Difco Ind., Detroit, Mich., USA) and incubated for a further 2 days at 30° C. Colonies were then sprayed with catechol in water (0.5 molar); 10 yellow/green colonies were selected and grown overnight in 10 ml of medium 1 plus 75 mM glucose and 1% w/v casamino acids at 30° C.

Cells were harvested, resuspended as above in phosphate buffer plus ethanol and incubated at 28° C. in the presence of 0.5 ml toluene as hereinbefore described. A constitutive mutant (D), less affected than mutant C by catabolite repression, was selected which gave an absorbance at 265nm of 61.2 (mutant C absorbance 15.6). Mutant D is also known as Pseudomonas putitda UV-4.

EXAMPLE 1

Synthesis Scheme

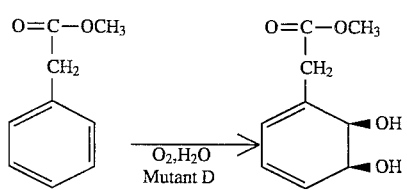

Step a

Mutant D culture containing 25 g dry cell weight of fresh highly active cells was added to 5 l of potassium phosphate buffer solution pH 7.5 containing 3 g/l of ethanol. The solution was maintained at pH 7.5 by occasional automatic caustic addition, at 28° C. and at 20% O2 saturation by air sparging and vigorous stirring. Neat methylphenyl acetate liquid was slowly added to the solution at 1 g/l/h over 10 hours. A rise in UV265 absorbance was seen over this time. At the end of the reaction the cells were separated by centrifugation and the pellets discarded. The supernatant was concentrated from 1.5% to 10% w/v solution by vacuum distillation at 40° C. To the concentrate (now 0.75 l) 0.75 w/v equivalent of MgSO$_4$ 7H$_2$O were added to precipitate biological debris material. This solution was filtered and the filtrate extracted three times with its own volume of ethyl acetate. The ethyl acetate solution was concentrated until all the solvent was removed.

The product was a light brown oil, 1-methoxycarbonyl methylene-2,3-cis(2R,3S)-dihydroxy-3,5-cyclohexadiene.

Step b

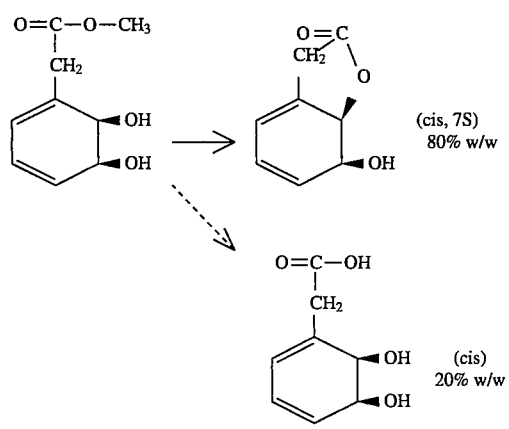

After several minutes at room temperature an exothermic crystallisation occurred. The resulting solid was triturated with n-hexane, collected on a filter and air dried. It was characterised by $^1$H NMR and mass spectrography as a 4:1 w/w mixture of compounds 7S-hydroxy-cis-dihydrocoumaran-2-one (II) and 2R,3S-dihydroxy-2,3-dihydrophenylacetic acid (V) (1.5 g; yield 30%).

7S-hydroxy-cis-dihydrocoumaran-2-one $^1$H NMR(CDCl$_3$) δ:4.65 (1H, t); 5.02 (1H, dd, J=3Hz); 3.30 (2H, dd, J=22.5Hz); 6.0 (2H, m); 5.90 (1H, m). $^{13}$C (CDCl$_3$) δ: 64.3; 81.6; 136.5; 125.6; 128.7; 114.9; 28.3; 164.4. MS$^m$/z: 152; fragments at 124 and 95

2R,3S-dihydroxy-2,3-dihydrophenylacetic acid

1HNMR (CDCl$_3$) δ: 5.02 (1H); 4.57 (1H, dd, J=5Hz); 2.65 (2H, S); 6.0 (2H, m); 5.8 (1H, m). $^{13}$C (CDCl$_3$) δ: 66.1; 82.0; 16.1; 112.0; 120.3; 33.09; 174.3.

Step, c: Preparation of 2-coumaranone (a) 1 g of the product of step b was dissolved in mesitylene, heated to 165° C. for 30 min, allowed to cool and isolated by extracting into water and then back into ethyl acetate. 2-coumaranone (VI) was isolated (0.8 g, yield 90%).

(b) Alternatively 1 g of the product of step b was heated as the solid to 150° C. to form the 2-coumaranone (VI). 1 g of the product of step b was treated with polyphosphoric acid at 150° C. to form the 2-coumaranone (VI) in 70% yield.

EXAMPLE 2

Synthesis Scheme

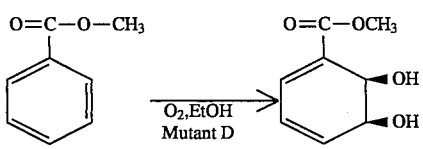

Mutant D culture containing 20 g dry cell weight of fresh, highly active cells was added to 4l of potassium phosphate buffer solution pH7.5 containing 4 g/l of ethanol. The solution was maintained at pH 7.5 by occasional automatic caustic addition at 28° C. and at 20% O$_2$ saturation by air sparging and vigorous stirring. Neat methyl benzoate was added slowly to the solution at 0.25–0.5 g/l/hour over 8 hours. A rise in UV 265 absorbance was seen, and GLC indicated no accumulation of substrate methyl benzoate over this time. At the end of the reaction the cells were separated by centrifugation and the pellets discarded. The supernatant was concentrated from 0.5% to 10% w/v solution by means of vacuum distillation at 20° C. To the concentrate (now 200 ml) 0.75 w/v equivalents of MgSO$_4$.7H$_2$O were added to precipitate biological depris material. This solution was filtered and the filtrate extracted three times with its own volume of ethyl acetate. The ethyl acetate solution was concentrated until all the solvent was removed. The product was an oil, methyl-2R,3S-dihydroxy- 2,3-dihydrobenzoate (9 g). The yield was 45% based on 16 g(0.117moles) methyl benzoate. $^1$HNMR(CDCl$_3$300MHz)δ: 3.0 (2H, brs, OH); 3.85 (3H, s,OMe); 4.52 (1H, dt, J=6.4,2.2); 4.62 (1H, d, J=6.4), 6.13 (1H, ddd, J=9.6,5.5,2.2); 6.25 (1H, dm, J=9.6); 7.1 (1H, d, J=5.5) MS$^m$/z(Cl): 170(M$^+$) [α]$_D$: +58.7° (c=1, CH$_2$Cl$_2$)

We claim:

1. A cyclohexadiene compound of formula (I) or (II)

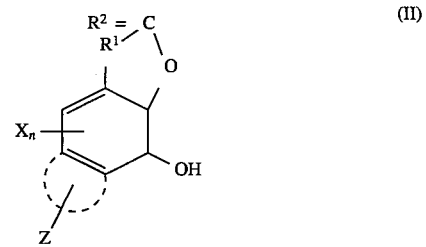

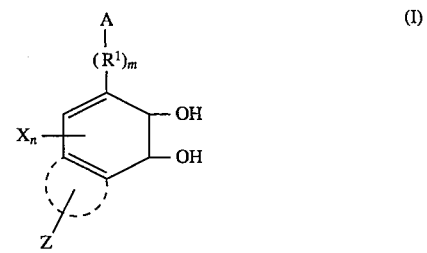

wherein A is C(O)—O—R where R is alkyl linked to the ring or R by the carboxylic group, or A is CN; R$^1$ is lower alkylene in formula (II) and methylene in formula (I) both optionally carrying one or more non-interfering substituents; R$^2$ is O or NH or NR$^3$; R$^3$ is C$_{1-4}$ alkyl; X is a non-interfering substituent; Z is an optional group comprising a 5- or 6-membered carbocyclic ring which is optionally substituted; m is 0 or 1; and n is 0–3; provided that when A is CN and n is 0 and Z is not present, then R$^1$ is methylene and m is 1, and further provided that when m is 0, and Z is not present, the carboxylic ester is not —C(O)—O-tertiary-butyl.

2. A cyclohexadiene compound of formula (I) according to claim 1 wherein R is $C_{1-10}$ alkyl.

3. A cyclohexadiene compound according to claim 1 or 2 wherein $R^1$ is —$CH_2$—, $CH_2CH_2$— or —CH(OH)—.

4. A cyclohexadiene compound according to claims 1 or 2 wherein m is 0.

5. A cyclohexadiene compound of formula (II) according to claims 1 wherein $R^2$ is O.

6. A cyclohexadiene compound according to claim 1 wherein Z is not present in formula (I) or (II).

7. A cyclohexadiene compound of formula (I) according to claim 1 wherein A is —C(O)—O—R; R is —$C_{1-10}$ alkyl, $R^1$ is methylene optionally substituted with halogen, —$C_{1-6}$ alkyl, —$C_{3-6}$ cycloalkyl, —$CF_3$, —CN, —$NO_2$, phenyl optionally substituted with a substituent X, —$CO_2R$, —OH, —$OR^4$, —SH, —$SR^4$, —$NHR^4$, —$NR^4R^4$, =O, =NOH, =$NOR^4$, —$CH_3$, =$CR^4H$ and =$CR^4R^4$; $R^4$ is —$C_{1-6}$ alkyl optionally substituted with halogen, alkoxy or alkylsulphide, or $R^4$ is —$C_{2-6}$ alkylcarbonyl; X is selected from the group, halogen, —$C_{1-6}$ alkyl, —$CF_3$, —CN, —$NO_2$, phenyl, —$CO_2R^4$, —OH, —$OR^4$, —SH, —$SR^4$ nd —$NR^4R^4$; n is 0–3 and Z is optionally the group benzene.

8. A cyclohexadiene compound according to claim 7 wherein R is methyl, m is 1, $R^1$ is —$CH_2$— or —CH(OH)—, and either n is 0 or when n is greater than 0 at least one X is halogen.

9. A cyclohexadiene compound according to claim 1 or 7 wherein m is 0, R is methyl and either n is 0 or when n is greater than 0 at least one X is halogen.

10. A cyclohexadiene compound of formula (II) according to claim 1 wherein $R^1$ is $C_{1-4}$ alkyl optionally substituted with halogen, $C_{1-6}$ alkyl, $C_{3-6}$ cycloalkyl, —$CF_3$, —CN, —$NO_2$, phenyl optionally substituted with a substituent X, —$CO_2R$ where R is —$C_{1-10}$ alkyl, —OH, —$OR^4$, —SH, —$SR^4$, =NH, =$NR^4$, —$NHR^4$, —$NR^4R^4$, =O, =NOH, =$NOR^4$, =$CR^4H$ and =$CR^4R^4$; is O, NH or $NR^3$; $R^3$ is methyl or ethyl; $R^4$ is $C_{1-6}$ alkyl optionally substituted with halogen, alkoxy or alkylsulphide or $R^4$ is $C_{2-6}$ alkylcarbonyl; X is selected from the group, halogen. $C_{1-6}$ alkyl, —$CF_3$, —CN, —$NO_2$, phenyl, —$CO_2R^4$, —OH, —$OR^4$, —SH, —$SR^4$, and —$NR^4R^4$; n is 0–3 and Z is optionally benzene.

11. A cyclohexadiene compound according to claim 10 wherein $R^1$ is —$CH_2$—or —CH(OH)—, $R^2$ is O and either n is 0 or when n is greater than 0 at least one X is halogen.

12. A cyclohexadiene compound of formula (I) or (II) according to claim 1:

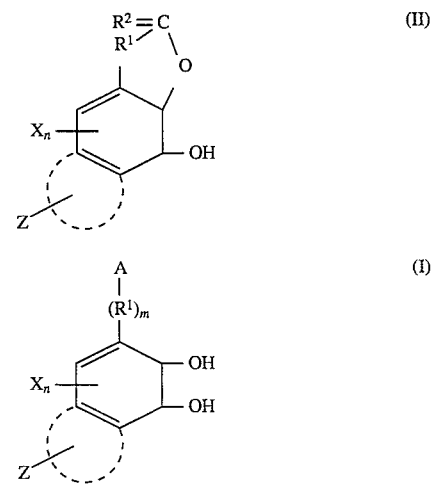

where A is a carboxylic ester linked to the ring or $R^1$ by the carboxylic group, or A is CN; $R^1$ is lower alkylene in formula (II) and methylene in formula (I) both optionally carrying one or more non-interfering substituents; $R^2$ is O or NH; X is a non-interfering substituent; and n is 0–3.

13. A cyclohexadiene compound according to claim 1 wherein the compound is the 2R,3S enantiomer.

* * * * *